United States Patent [19]
Price et al.

[11] Patent Number: 5,591,920
[45] Date of Patent: Jan. 7, 1997

[54] DIAGNOSTIC WIRE BOND PULL TESTER

[75] Inventors: Susanne F. Price, Berwyn, Pa.; Hiroshi Munakata, Yokohama, Japan; Eli Razon, Maple Glen, Pa.; Gil Perlberg, Elkins Park, Pa.; Igor Fokin, Warminister, Pa.

[73] Assignee: Kulicke and Soffa Investments, Inc., Wilmington, Del.

[21] Appl. No.: 560,529

[22] Filed: Nov. 17, 1995

[51] Int. Cl.⁶ .................................................. G01N 3/00
[52] U.S. Cl. ............................ 73/828; 73/827; 228/4.5
[58] Field of Search ........................... 73/828, 827, 806, 73/805, 831, 833

[56] References Cited

U.S. PATENT DOCUMENTS

3,840,169  10/1974  Steranko et al. ........................ 228/4
4,786,860  11/1988  Zimmerman .......................... 73/827
5,326,015  7/1994   Weaver et al. ........................ 228/102

Primary Examiner—Hezron E. Williams
Assistant Examiner—Ronald L. Biegel
Attorney, Agent, or Firm—John B. Sowell

[57] ABSTRACT

A novel pull strength tester is incorporated into an automatic wire bonder for performing pull strength tests during production bonding operation. The pull strength tester is provided with a control for automatically applying increments of pull force on a fine wire after making a bond. The control senses the elongation of the fine wire as a result of the force applied and is capable of terminating the pull test at a predetermined threshold value or continuing to increase the force until a break occurs. After each increase in force, a continuity circuit determines if the wire has broken at the bond or the bond has lifted off the bonding target. The system employs the information to determine if a proper bond was made and/or if a short tail was made which could affect the subsequent attempt to form a proper ball for a subsequent first bond.

17 Claims, 6 Drawing Sheets

DIAGNOSTIC WIRE BOND PULL TESTER

BACKGROUND OF THE INVENTION

1. Field of the Invention

The present invention relates to a monitor for monitoring the integrity of wire bonds while conducting bonding operations. More particularly, the present invention relates to testing the pull strength of first and/or second bonds during teach or during production operations.

2. Description of the Prior Art

When automatic high speed wire bonders are set up for bonding operations, it is known to bond an interconnecting wire and then place a "J" hook of a calibrated pull tester under the wire and to pull until the wire breaks or one or more of the bonds fail. The information gained from such manual intervention destructive tests enables maintenance personnel to achieve uniform acceptable bond strength for subsequent bonding operations.

After a wire bonder is set up for production operations, it is known to monitor for missing wires and/or non-stick bonds and to monitor bond quality. Such systems are shown and described in U.S. Pat. Nos. 4,558,596; 4,808,948 and 4,586,642 all of which are assigned to Kulicke & Soffa Industries Inc., the assignee of the present application.

The aforementioned patents are directed to systems that monitor either frequency or resistance to determine the continuity of an electrical pad indicative of a bonded wire. Other systems monitor frequency or resistance to determine the bond quality. None of the aforementioned bond quality monitoring systems are known to be capable of simultaneously monitoring bond strength and bond quality. All prior art pull strength tests require operator intervention.

Gold ball bonds made at a first bond position are usually stronger than wedge bonds made at a second bond position. The trend toward higher density integrated circuits on large chips has effectively decreased the size of the lead out pads on the semiconductor chip. This trend has generated a need for smaller ball bonds and special bonding tools for making fine pitch first and second bonds. The trends towards smaller non-conventional tools have created a need to monitor the bond strength because the smaller tools wear faster and smaller bonding tools usually result in lower bond strength. Applicants do not know of an apparatus or system that will non-destructively test bond strength and monitor tool wear during a bonding operation.

Accordingly, it would be desirable to provide a novel wire bond monitoring system which cooperates with a novel wire continuity monitoring system and an adjustable force application and monitoring system to detect changes in bonding operations which affect the pull strength of wire bonds made during production operations. It would be further desirable to selectively collect wire bond pull strength data during actual production on line operations which can be used to adjust bonding parameters which in turn produce optimum bond strength.

SUMMARY OF THE INVENTION

It is a primary object of the present invention to provide a system for an automatic wire bonder for testing the pull strength of first and/or second bonds during initial set-up or during teach operations as well as during continuous production bonding operations.

It is a another primary object of the present invention to provide a flexible and selectively programmable pull testing system in an automatic wire bonder.

It is a another primary object of the present invention to provide a system for making bond quality tests of bonds made during actual production operations.

It is a another primary object of the present invention to provide a pull test monitoring system capable of detecting numerous types of conditions which can affect wire bonds before the bonds deteriorate to an unacceptable standard.

It is a another primary object of the present invention to provide a novel pull tester which can be used to monitor production of gold ball bumps being made on semiconductor chips.

It is a another object of the present invention to provide a monitoring system for detecting bonding tool wear.

It is a general object of the present invention to provide a monitoring system for selecting, comparing and/or replacing bonding tools.

It is a general object of the present invention to provide a monitoring system for optimizing wire bonding tool strength and the speed of bonding operations.

According to these and other objects of the present invention, there is provided an automatic wire bonder of the type having a Z-drive motor for positioning a bonding tool during a wire bonding operation and also provided with a Z-height encoder and control means for applying predetermined increasing increments of current to said Z-drive motor. After a first and/or second fine wire bond is made, the bonding tool is raised a small distance above the bonding tool and the wire is clamped relative to the bonding tool. Control means apply an increasing total force on the fine wire in predetermined increments, thus is capable of determining whether a predetermined threshold pull strength is reached, or the sensed elongation of the fine wire is predictive of a wire ready to break, and/or is capable of confirming that a discontinuity or break in a fine wire at the device has occurred.

DESCRIPTION OF A PREFERRED EMBODIMENT

Figure 1:
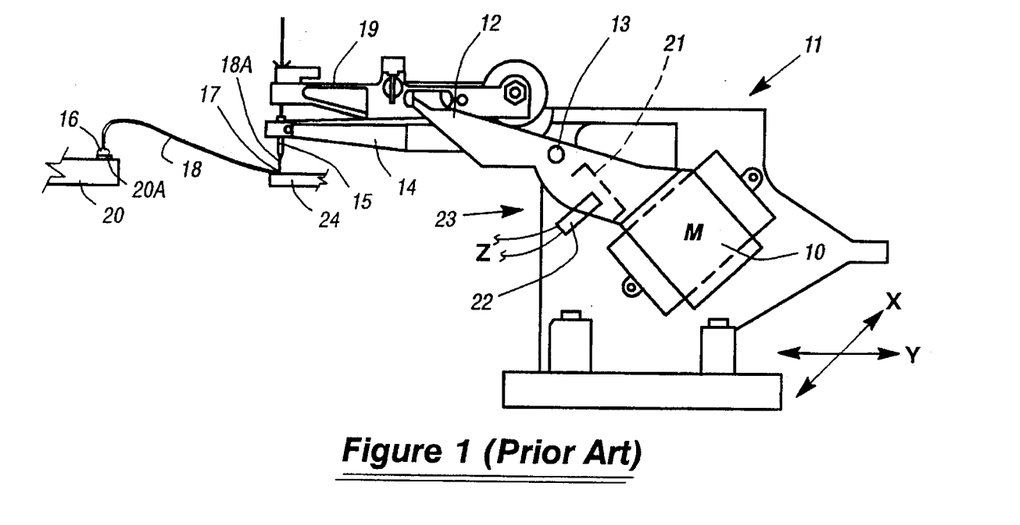
FIG. 1 is a schematic drawing and side view of a prior art Z-drive motor for positioning a bonding head which supports a wire clamp and a capillary bonding tool for use in an automatic wire bonder to make fine wire bond interconnections on a semiconductor device.

Refer now to FIG. 1 showing a schematic drawing of a prior art Z-drive motor 10 which is mounted on the bond head assembly 11. The Z-drive motor 10 is preferably a linear motor for moving a pivotal support structure 12 which supports a transducer 14 in which a bonding tool 15 is mounted. The pivotal support 12 also supports wire clamps 19 which pivot about pivot axis 13. The bond head assembly 11 is preferably mounted on an X-Y table (not shown) for effecting movement of the bonding tool 15 so as to make a first ball bond 16 on a lead out pad 20A of a semiconductor device 20 and for forming an interconnecting fine wire 18 terminating in a second bond 17 on a lead frame or carrier 24. After making a second bond, the bonding tool 15 is raised vertically to pay out a tail 18A before closing the wire clamps 19 and continuing to move in an upward direction to break the fine wire 18A at the second bond 17 leaving the tail 18A as described in numerous patents and publications concerning ball bonding operations. The pivoting support structure 12 is provided with a movable element 21 of an encoder which cooperates with a fixed element 22 on the bond head assembly 11. In the preferred embodiment of the present invention, the Z-encoder 23 may be a sound encoder or proximeter or preferably a highly precise gradient scale and sensor. After breaking the tail 18A at the second bond 17, the end of the tail is raised to a reset height and heated by an electronic flame off to form a new ball for the next fine wire interconnection. When the tail 18A is not of a proper length, the EFO equipment (not shown) is not capable of making a proper size ball for the next first bond. One of the purposes of the present invention is to assure that the tail 18A is made of a proper length so that the ball for a next first bond is made of proper size.

Figure 2:
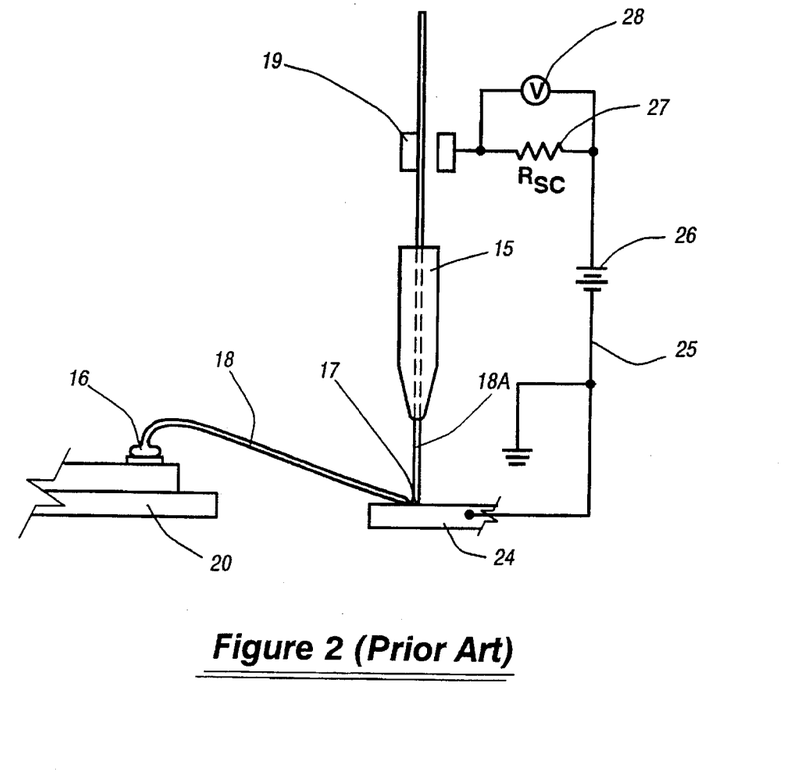
FIG. 2 is a schematic drawing and side view of a prior art analog electrical circuit used to check continuity.

Refer now to FIG. 2 showing a schematic drawing and side view of a prior art electrical circuit used to check continuity. After the first bond 16 is made on a semiconductor device and the wire 18 is paid out to a second bond position and a second bond 17 is made, the bonding tool 15 is raised to a tail height paying out a proper length of tail 18A. The wire clamps 19 are shown engaging the fine wire 18A so that a series circuit is formed from the second bond 17 through the lead frame 24 through the grounded circuit lead 25 and through the voltage source 26 and a scaling resistor 27 across which is placed a voltage monitor 28 in the return path to the wire clamps 19. Thus, it will be understood that if the second bond 17 is properly attached to the carrier 24, there is an electrical path through the aforementioned circuit which may be detected and monitored at the monitor 28. When the monitor 28 indicates that a proper bond has been made, it is also indicative that the proper length of tail 18 has been made and the next sequence of testing operations may be performed to assure that the tail breaks at the second bond and does not come loose, making a lift off or discontinuity.

Figure 3:
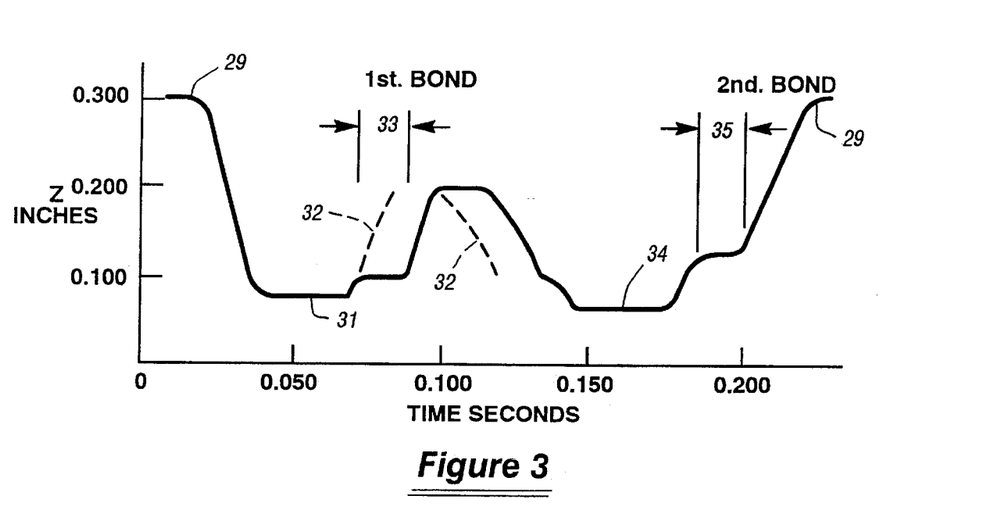
FIG. 3 is waveform diagram of time versus vertical height for a capillary bonding tool when conducting bonding operations and showing the time used for pull test operations at a first and a second bond.

Refer now to FIG. 3 showing a waveform diagram of time versus vertical height of a capillary bonding tool when conducting a bonding operation. The bonding tool starts from a reset height 29 and drops to a first bond position contacting the semiconductor device at point 31. After making the first bond 16, the bonding tool would be raised to a kink or loop height to feed the wire out prior to making a second bond. If no pull test is to be performed, the bonding tool trajectory is shown at point 32 in phantom lines, however, when conducting the pull test operations, the wire is clamped above the first bond 16 and a pull test operation is performed during the time period shown as 33. Similarly, after conducting the first bond test operation, the bonding tool is repositioned to point 34 to make a second bond 17. After making a second bond the tool is raised to its tail height where the wire clamps are closed and the second pull test operation may be performed during the time period 35 before proceeding to reset height 29 after breaking the wire at the second bond to form a tail for the next sequence of bonding operations. It will be understood that the present invention bond testing operation is actually conducted during the bonding operation which forms an interconnecting wire. The time penalty for performing this on-line or real-time testing operation is shown by the time zones 33 and 35. It is desirable to only conduct the pull test on less than all of the wire bonds which are made when bonding a semiconductor device. For example, a semiconductor device may have as many as 300 individual interconnecting fine wires from the semiconductor device to the carrier. By conducting pull tests on only 5 or 10% of the interconnecting leads at first and second bonds, it is possible to determine bond quality as well as tool wear. In the preferred embodiment of the present invention, the pull test operation described hereinafter is always performed during teach and setup operations to determine the optimum pull strength and bond quality for subsequent operations.

Figure 4:
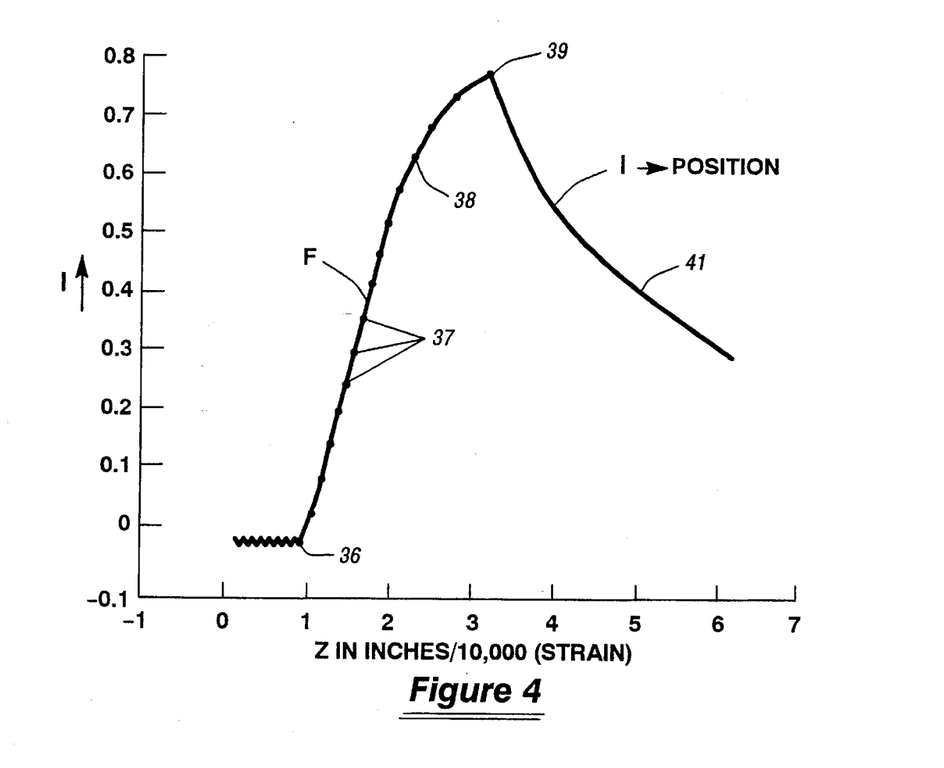
FIG. 4 is a stress versus strain diagram for a fine bonding wire being stressed to failure when conducting a destructive pull test sequence of operations.

Refer now to FIG. 4 showing a stress versus strain diagram for a piece of fine wire when being stressed to failure after conducting a second bond. The values shown are for a 1 mil gold wire. After making the second bond at 36 and raising the bonding tool to a tail height and closing the wire clamps, it is now possible to increase the current applied to the Z-drive motor 10 so as to increase the pull force on the bonding wire. At predetermined sequential times, fixed levels of current are applied in increasing increments to Z-drive motor 10 as shown at points 37. Initially the stress strain diagram is substantially linear until it reaches a distortion point shown at approximately point 38 where the elongation for the same increment of current causes a larger increase in strain or elongation. This increased elongation can be detected as will be described hereinafter. It is possible to sense or determine point 38 before any break occurs at break point 39. Between the points 36 and 39, the linear motor 10 is in a force mode attempting to apply increasing pull strength to the fine wire 18 and 18A. When the break point 39 is reached, the tool holder would rapidly accelerate in an upward direction unless the total force or current applied to the linear motor is reduced. Thus, anticipating point 39, the linear motor 10 is placed in a position mode where the current applied along the curve shown at 41 is only sufficient to balance the bonding tool holder and transducer in a desired level position as will be explained hereinafter.

Figure 5:
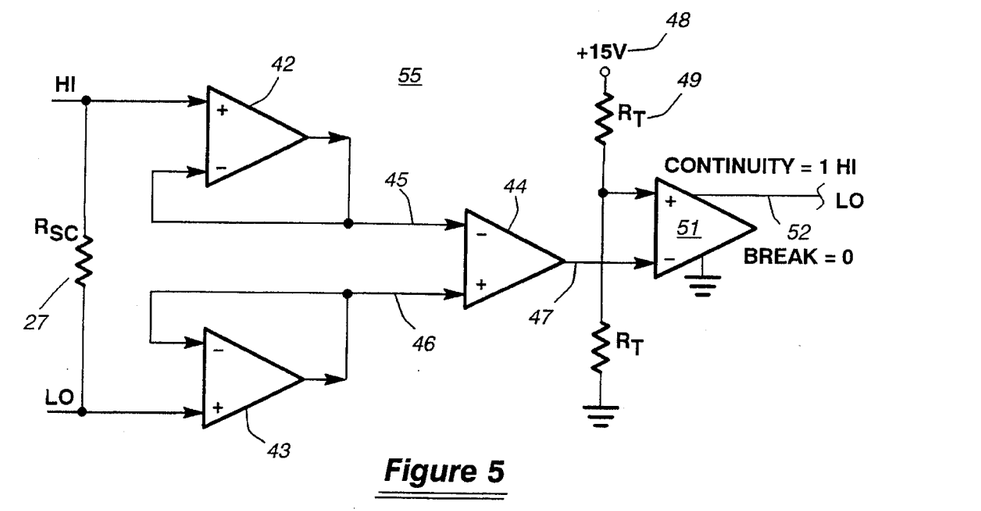
FIG. 5 is a schematic circuit drawing of a digital continuity circuit used to detect a discontinuity or break between a fine wire and a semiconductor device.

Refer now to FIG. 5 showing a schematic circuit drawing of a digital continuity circuit used to detect when a discontinuity or break occurs between the fine wire and the carrier 24 at the second bond 17. The scaling resistor 27 described in the circuit of FIG. 2 is shown in the circuit in FIG. 5. A voltage across resistor 27 is applied to a pair of opamps 42 and 43 to produce outputs on lines 45 and 46 that are applied to a operational amplifier 44. The output of amplifier 44 on line 47 is applied to a negative input of a high gain comparator amplifier 51 which has a positive input from a threshold resistor 49. A voltage source 48 is connected to ground across divide resistors $R_T$. An output on line 52 produces two levels shown as continuity equals one and break equals zero. This digital output will be used in the circuit to be describe hereinafter to effectively monitor the pull strength and other factors which affect bonding operations.

Figure 6:
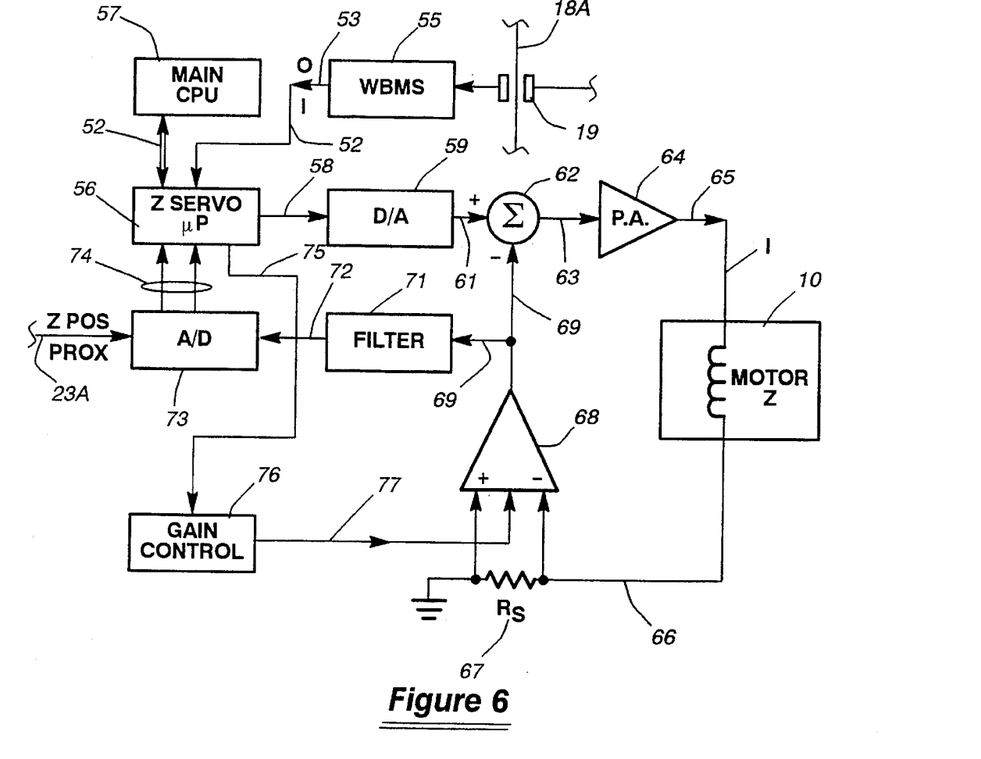
FIG. 6 is a schematic circuit drawing of the present invention automatic wire bonder monitoring system (WBMS) and main computer control coupled to a Z-drive motor for applying increments of a pull force to a fine wire when conducting a pull test sequence of operations.

Refer now to FIG. 6 showing a schematic circuit diagram of the present invention automated wire bonder monitoring (WBMS) 55 and a main computer control coupled to a Z-drive motor and a Z-servo microprocessor for applying increments of pull force to a fine wire when conducting the aforementioned pull test sequence of operations. The main processor 57 initiates commands on line 52 and receives information from the Z-servo microprocessor 56 on the same line. The aforementioned WBMS 55 generates a high or a low signal on line 52 indicative of continuity or no continuity and this information is supplied to the Z-servo microprocessor. The Z-servo microprocessor 56 initiates a digital number on line 58 which is indicative of a desired force. The digital information is converted in D to A converter 59 to an analog signal on line 61 which is indicative of the desired current to be applied to the Z-drive motor 10. The signal is applied to a summing circuit or a summing balance circuit 62 which generates a difference signal on line 63 which is applied to the power amplifier 64 whose output on line 65 is the current applied to the Z-drive motor 10. The actual current on line 66 is passed through a current sensing resistor 67 to ground. The differential voltage across the current sensor resistor 67 is applied to an instrumentation amplifier 68 which generates an actual current signal on line 69 which is applied to the negative input of the summing circuit 62. The summing circuit then generates the difference current sensed on line 63. This loop continues until it cancels out the Z-error. The same actual current on line 69 is applied to a filter 71 which strips off the high frequency noise before applying the actual current signal to the A to D 73. The A to D converter is shown having two output lines 74 which are applied to the Z-servo microprocessor 56. One line 74 is indicative of the actual current (I) and the second line 74 is indicative of the Z-position indicated by the proximeter 23 on line 23A.

The Z servo microprocessor 56 increases current on line 58 while monitoring continuity from the WBMS on line 52 looking for a break. When the break occurs, the signal on line 52 is applied to the Z-servo 56 and the Z-servo reads the current (I) was which caused the break. The current (I) on line 74 is indicative of the force that was required to cause the break. It is also possible to read the Z-position when the break occurs from the information applied from the Z proximeter on line 23A. Since the same circuit shown in FIGS. 6 is used for contact detection on touchdown, the sensitivity of the circuit must be changed for pull test operations. To accomplish this change, the Z-servo microprocessor 56 generates a signal on line 75 to the gain control 76 which increases the sensitivity by generating a signal on line 77 which is applied to the instrumentation amplifier 68. After the pull test operation is completed, the gain control signal is no longer required and is returned to normal sensitivity. Thus the system shown may be viewed as a dual sensitivity system.

Figure 7:
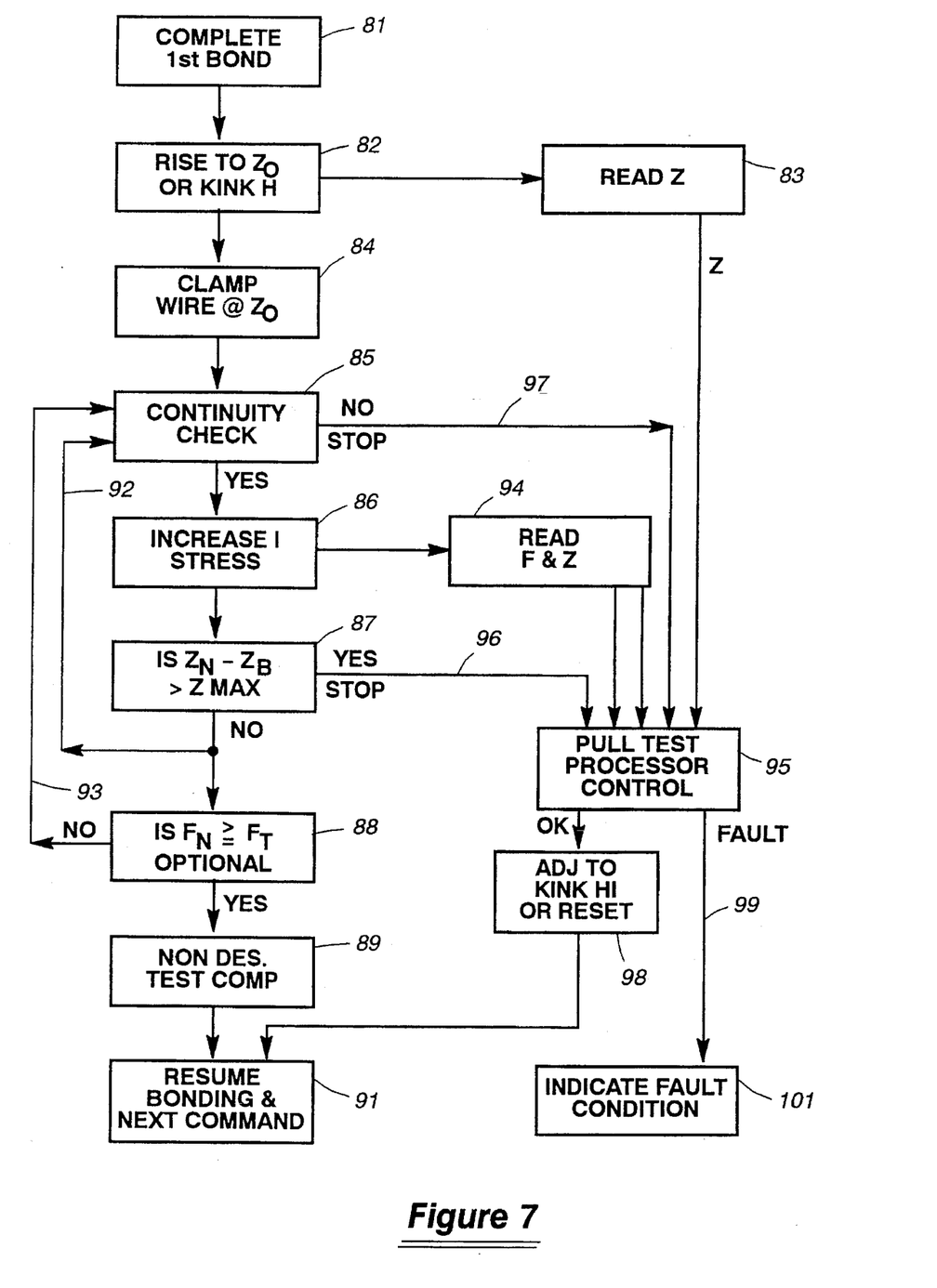
FIG. 7 is a block diagram of major steps employed when conducting a non-destructive pull test sequence of operations at first or second bond employing the system shown in FIG. 6.

Refer now to FIG. 7 showing a block diagram of the major steps employed when conducting a non-destructive pull test sequence operations at a first bond employing the system shown in FIG. 6. The first bond 16 is shown being completed at block 81. The next step is to raise the bonding tool 15 to a $Z_0$ predetermined height or kink height as shown in block 82. At this point, the Z-height is read as shown at block 83. After rising to kink height, the wire clamps 19 are closed as shown at block 84. A first continuity check is preformed subsequently at block 85. If the continuity check is positive and the wire clamps are closed, it is now possible to increase the pull strength by increasing an increment of current to the Z-drive motor 10 as explained hereinbefore and shown at block 86. After applying the new pull strength force, a comparison test is made at block 87 which effectively determines whether the Z-height now minus the Z-height before has increased to the point where it equals a predetermined a Z maximum which occurs between points 38 and 39 as shown in FIG. 4. If the pull force is still performing correctly, the elongation is on the linear portion of the curve shown in FIG. 4 by points 37 and it is possible to make the next logical test is optional as shown at block 88. Since this is a non-destructive test, block 88 determines if the force now is equal to or greater than a threshold force which is predetermined to prevent breakage and maintain a desired force on the linear portion 37 of the force curve shown in FIG. 4. If the desired force has been reached, it is now possible to terminate tests at block 89 and to resume bonding as shown at the logic block 91.

Referring back to block 87, when the output of block 87 indicates that the stress is still on the linear portion of the force curve along points 37 and the threshold force has not been reached, it is possible to loop back through loop 92 to perform a continuity check and to increase the stress until the Z-elongation reaches the points on the curve of FIG. 4 between points 38 and 39 or a threshold force is reached which will also terminate the testing operation. The threshold force at block 88 is shown as an optional condition but will allow the operator to stay in a loop until a desired threshold force is reached. At each point when the stress is increased as shown at block 86, the force and the Z-position is preferably read at block 94 and applied to the pull test processor control 95. When the non-destructive test is performed at block 87 and the logic indicates that increased elongation Z has occurred at point 38 of FIG. 4, a signal on line 96 is generated to terminate the pull test and to avoid destruction of the wire. Even though the maximum Z-height may be reached, it is desirable to perform a continuity check at block 85 via loop 93 to determine if a discontinuity has occurred on line 97 indicative of the first bond being lifted off of its target. The information supplied via lines 96 and 97 in block 83 and 94 is applied to the test pull tester processor control 95 which can determine whether to continue bonding as shown as the output on the line to block 98 or whether some fault condition has occurred as shown on line 99 which will initiate some form of alarm or fault condition as shown at block 101.

Figure 8:
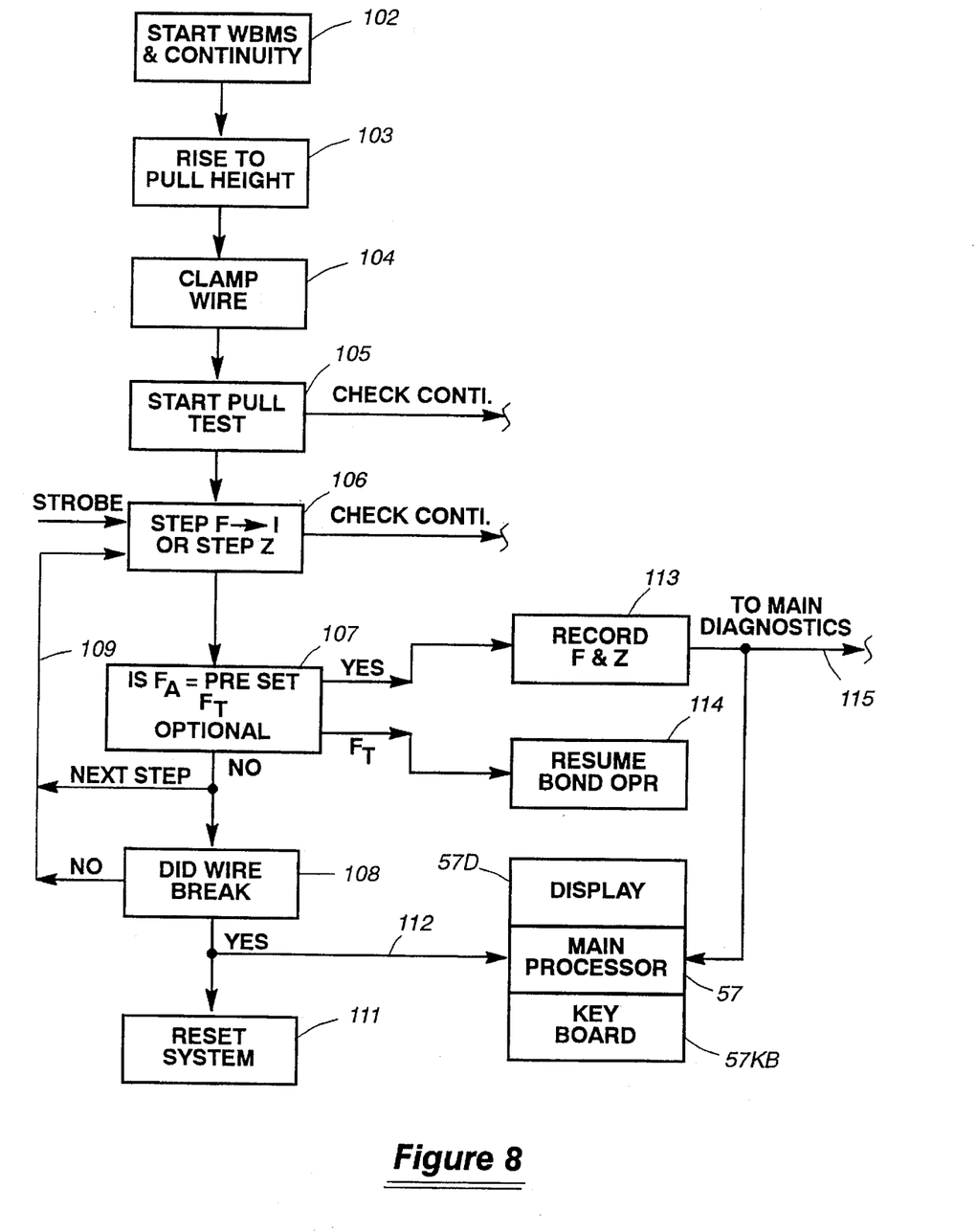
FIG. 8 is a simplified block diagram showing major steps employed when conducting a destructive pull test sequence of operations.

Refer now to FIG. 8 showing a simplified block diagram of the major steps employed when conducting a destructive pull test sequence of operations, especially for diagnostic operations. The destructive test starts when the wire bond monitoring system and continuity checking systems are initiated as shown at block 102. The bonding tool 15 is raised to a pull height after a bond is made as shown at block 103, then and the wire clamps are closed as shown at block 104. At this point the pull test can start as shown at block 105 and a continuity test is made at this point as explained hereinbefore. After the pull test starts it is now possible to step the force by increasing increments of current as shown at block 106 or to make predetermined Z-steps for special operations as shown at block 106. In either case, the continuity is again checked. Had the continuity failed at either block, it would have indicated that the test was completed and a wire break or destruction of the bond had occurred in some manner. If the bond has not been destroyed or the wire broken, it is possible to form an optional operation at block 107 (which will be explained in greater detail hereinafter) to determining if the force applied is equal to a preset threshold force $F_T$. This block, if eliminated, allows performance of the aforementioned destructive test where the logic of the monitoring system determines if the wire is broken as shown at block 108. If the wire breaks, the system defers to block 111 where the system must now be reset. The output of the optional block 107 on line 109 has a loop back which continues to step the force or Z-system until the desired result is obtained by breaking the wire as shown at Block 108. If the block 108 indicates that the wire is not yet broken, it also forms a loop back on line 109 to continue to increase the force of the Z-steps until the wire does break. At the output of block 108 on line 112, the main processor 57 is informed of the break condition and the processor can either shut down or go into an idle state awaiting the next command or instruction. The state is shown on display 57D and this may be changed or continued by using the keyboard 57KB. In the optional block 107, it is possible to reach a threshold FT where the wire is not completely broken but is stretched to the point where the device or wire is not a usable wire or device. At this point, it is possible to defer to block 113 and record the force and the Z-position and send this to a diagnostic memory as shown on line 115. If the wire is destroyed but not broken, it is possible to resume the bonding operation as shown at block 114 and continue to collect information for diagnostic purposes which is applied to line 115 and sent to the main processor.

Figure 9:
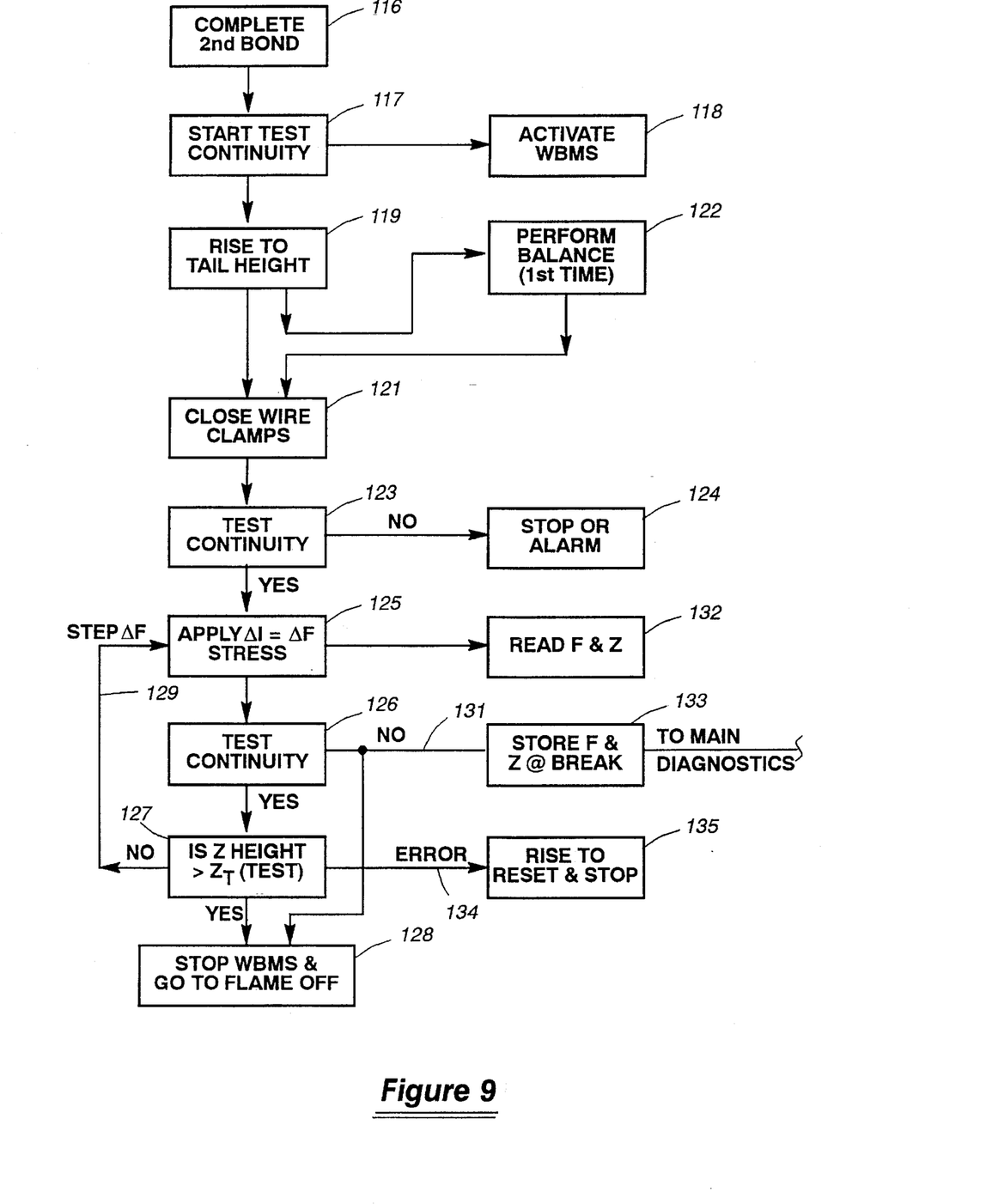
FIG. 9 is a more detail block diagram of the major steps employed when conducting a sequence of pull test operations at second bond to confirm that a strong second bond and a proper tail length has been made.

Refer now to FIG. 9 showing a more detailed block diagram of the major steps employed when conducting a sequence of pull test operations at second bond. The information which is gained by conducting this pull test will confirm whether a second bond has been made, whether a proper tail length has been made and will provide information indicative to tool wear. After the second bond has been completed as shown at block 116, a continuity test is performed at block 117 and at the same time, the wire bonding system is activated as shown at block 118. The bonding tool is then raised to tail height as shown at block 119 and the wire clamps are closed as shown at block 121. When the first pass is made through the logic blocks from block 119 to 121, it is preferred that a one time only balance operation is performed as shown at block 122. The balance operation determines what current force is necessary to be applied to the linear motor 10 to maintain the bonding tool at desired Z position for the desired tail length. This information is stored in the memory associated with the Z-servo processor 56 or may be stored in the main memory of the main CPU 57. With the wire clamps now closed as shown at block 121, a continuity test is performed as shown at block 123 which may fail and indicate that a wire has already broken before the pull forces are applied as shown at block 124. If the tail is bonded to the carrier or substrate, the continuity test is positive and it is possible to now start applying increments of current which are indicative of predetermined increments of force as shown in block 125. After the application of each increment of force, a new continuity test is conducted as shown at block 126. If continuity continues positive, the test proceeds to the logic shown at block 127 which determines if the Z-height now is greater than the desired threshold Z or test height to be used to terminate the test operation. If the test height is reached in block 127, then the wire bonding system must prepare the wire by flaming off and forming a ball for the next sequence of operations as shown at block 128. If the desired Z-height has not been reached, the logic on line 129 loops back and applies another increment of force to continue the pull test operation. Thus, it will be understood by observing the three blocks 125 through 127 that a force will be reached which will break the wire 18 at second bond 17 and these forces are only determined when the continuity test 126 indicates a discontinuity on line 131. Before the discontinuity, the force and Z position is read at block 132 and after the discontinuity occurs, the force and Z-position indicative of a break are stored and applied to the diagnostic memory at block 133 even though these two blocks may be the same.

At block 127 when a determination is made that a threshold Z-height has already been reached with low force this may indicate excessive tool wear and an error condition which is indicated by a signal on line 134. When this condition occurs, it is possible to rise, the bonding tool and stop and indicate to the operator that the tool is worn and should be replaced as shown in block 135.

Having explained a preferred operation of the pull test operation at second bond, it will be understood that the pull tester has performed a test which will indicate whether the second bond shown as a wedge bond has enough strength or is strong enough to permit the automatic wire bonder to pay out a full length tail and also will determine if the proper tail length has been made. While conducting these operations, it is also possible to determine if the bonding tool is wearing to the point where a strong second bond has not been made and requires replacement. Further, at block 127 when the Z-height is tested it is possible to determine through the information applied to the controller whether lift off of the second bond has occurred.

Having explained a preferred embodiment of the present invention and several modifications and alterations, it is also possible to reconfigure the programs using the logic block shown in FIGS. 7 through 9 to perform additional diagnostic operations.

It is now apparent that the present invention may be employed to prevent an automatic wire bonder from attempting to make a wire bond without a proper tail or wire in the capillary. Further, the present invention can determine the expected life of a capillary before replacement is required which further enhances the mean time between failure. The present invention can also determine the best capillary for longest life between different types of capillaries. When the present invention is used as an on-line monitor, it is not necessary to monitor every bond or even monitor every device. The same information can be obtained when monitoring as few as every 100th device even though as many as 5 to 10 percent of the leads may be monitored during initial set-up.

What is claimed is:

1. A wire bond tool strength tester for automatic wire bonders, comprising:

an automatic wire bonder of the type having a bonding head assembly for supporting a tool holder for positioning a bonding tool in a Z axis for making fine wire bonds, a Z-axis encoder coupled to said bonding head assembly for monitoring the Z-axis position of the bonding tool in said bond tool holder, a Z-axis drive motor for raising said bonding tool in a Z direction above a fine wire bond, wire clamping means for clamping a fine wire extended above said fine wire bond, control means for applying predetermined increments of pull force in increasing steps to said fine wire through said wire clamping means, a continuity circuit coupled to said fine wire for determining the continuity of the fine wire bond at said pull force step, means for recording the Z position of said bonding tool and the pull force being applied to said fine wire at said predetermined pull force steps, and means for determining the pull force applied to said fine wire bond when a predetermined condition of stress or strain or continuity has been reached.

2. A wire bond pull tester as set forth in claim 1 wherein said means for determining the pull force comprises means for detecting a pull force indicative of the elastic limit of said fine wire.

3. A wire bond pull tester as set forth in claim 1 wherein said fine wire bonds comprised a first ball bond, and said control means further includes means for setting a first threshold force level that is less than the force needed to break said fine wire above said first ball bond.

4. A wire bond pull tester as set forth in claim 3 wherein said control means further includes means for determining that a first threshold force has been reached, and logic means for continuing bonding operations when said threshold force level has been reached.

5. A wire bond pull tester as set forth in claim 2 wherein said control means for applying said predetermined increments of pull force to said fine wire includes means for raising said pull force to the point where the wire breaks at a first bond.

6. A wire bond pull tester as set forth in claim 1 which further includes means for recording and displaying the increments of pull force applied and the corresponding Z position which occurs during pull test.

7. A wire bond pull tester as set forth in claim 2 wherein said fine wire bonds comprise a second or wedge type bond, and said control means further include means for applying said predetermined increments of pull force for breaking said fine wire at said second bond.

8. A wire bond pull tester as set forth in claim 6 wherein said control means for applying said predetermined increments of pull force comprises a microprocessor having digital output signals for generating a current to be applied as said Z-axis drive motor.

9. A wire bond pull tester as set forth in claim 8 where said means for applying predetermined increments of pull force comprises a digital to analog converter coupled to the output of said microprocessor, and a power amplifier coupled to the output of said digital to amplifier converter and to an input of said Z-drive motor.

10. A wire bond pull tester as set forth in claim 8 wherein said control means for recording the Z position of said bonding tool comprises a main processor coupled to said servo motor microprocessor.

11. A wire bond pull tester for automatic wire bonders of the type which includes a Z-drive motor for positioning a bonding tool during continuous bonding operations, comprising:

a bonding head for positioning a bonding tool, a Z-axis encoder coupled to said bonding head for monitoring the Z-axis position of said bonding tool, a fine wire threaded through said bonding tool for making first and second bonds between a semiconductor device and a carrier, wire clamping means for clamping said fine wire after making a second bond on said carrier, continuity circuit means coupled to said fine wire through said wire clamping means, control means for applying increasing increments of pull force through said wire clamping means and for sensing the amount of elongation of said fine wire between said wire clamping means and said second bond, and means for determining the Z-axis position of said bonding tool when said continuity circuit means indicates a break has occurred in said fine wire above said second bond.

12. A wire bonding tool tester as set forth in claim 11 wherein said control means further include means for determining the pull force that cause the break in said fine wire and further includes means for terminating said pull force on said fine wire.

13. A wire bond pull tester as set forth in claim 12 wherein said control means further includes means for determining the length of the fine wire tail extending from said bonding tool.

14. A method of performing pull test on a fine wire during a bonding operation by an automatic wire bonder, comprising the steps of:

bonding a fine wire to a target on a device with a bonding tool, raising the bonding tool to a predetermined distance above the bond on the bonding target while paying out fine wire, clamping the fine wire with wire clamps fixed relative to the bonding tool, connecting a continuity circuit between said wire clamps and said bonding target, applying predetermined increments of pull force to said wire clamps, reading said increments of pull force applied to said fine wire in said bonding tool as a result of an increase in total pull force, and continuing to pull said fine wire through said wire clamps by increasing the total pull force in predetermined increments of pull force until said fine wire breaks or a predetermined pull force is reached.

15. The method as set forth in claim 14 wherein said pull tests comprises the steps of setting a desired threshold pull force, and comparing the total pull force with said threshold pull force to determine if the pull test is completed.

16. The method as set forth in claim 15 which further includes the steps of completing said predetermined pull test before said fine wire is disconnected from said bonding target at a first bond.

17. The method as set forth in claim 15 which further includes the step of completing said predetermined pull force by disconnecting said fine wire from said bonding target at a second bond after a predetermined threshold pull force is reached.

* * * * *